United States Patent
Candau

(10) Patent No.: US 6,875,426 B2
(45) Date of Patent: *Apr. 5, 2005

(54) SELF-TANNING COMPOSITION CONTAINING A TETRAHYDROCURCUMINOID AND A SELF-TANNING AGENT

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 33 days.

This patent is subject to a terminal disclaimer.

(21) Appl. No.: 10/400,551

(22) Filed: Mar. 28, 2003

(65) Prior Publication Data

US 2003/0228268 A1 Dec. 11, 2003

Related U.S. Application Data

(60) Provisional application No. 60/377,958, filed on May 7, 2002.

(30) Foreign Application Priority Data

Mar. 28, 2002 (FR) .............................. 02 03934

(51) Int. Cl.⁷ ............................ A61K 7/42; A61K 7/44; A61K 7/00
(52) U.S. Cl. ......................... 424/59; 424/60; 424/400; 424/401
(58) Field of Search ........................... 424/59, 60, 400, 424/401

(56) References Cited

FOREIGN PATENT DOCUMENTS

| EP | 0 903 342 A1 | 3/1999 |
| EP | 1 092 415 A2 | 4/2001 |
| WO | WO 97/35842 A1 | 10/1997 |

OTHER PUBLICATIONS

Search Report issued in French Priority Counterpart FR 02/03934, issued on Dec. 6, 2002, 2 pages.

*Primary Examiner*—Shelley A. Dodson
(74) *Attorney, Agent, or Firm*—Burns, Doane, Swecker & Mathis, L.L.P.

(57) ABSTRACT

The present invention relates to a cosmetic and/or dermatological composition more particularly intended for artificially tanning and/or browning the skin and comprising, in a cosmetically acceptable support, at least one derivative or a mixture of derivatives of 1,7-bisphenyl heptane-3,5-dione of particular structure and at least one self-tanning agent.

The present invention also relates to a cosmetic treatment process for artificially tanning or browning the skin and to the use of at least one derivative or a mixture of derivatives of 1,7-bisphenyl heptane-3,5-dione of particular structure for improving the coloration and/or stability of a self-tanning agent.

The invention also relates to the uses of these compositions for giving the skin a coloration close to that of a natural skin tan.

28 Claims, No Drawings

SELF-TANNING COMPOSITION CONTAINING A TETRAHYDROCURCUMINOID AND A SELF-TANNING AGENT

CROSS-REFERENCE TO PRIORITY/PROVISIONAL APPLICATIONS

This application claims priority under 35 U.S.C. § 119 of FR-02/03934, filed Mar. 28, 2002, and of provisional application Ser. No. 60/377,958, filed May 7, 2002, both hereby expressly incorporated by reference.

BACKGROUND OF THE INVENTION

1. Technical Field of the Invention

The present invention relates to a cosmetic and/or dermatological composition more particularly intended for artificially tanning and/or browning the skin and comprising, in a cosmetically acceptable support, at least one derivative or a mixture of derivatives of 1,7-bisphenyl heptane-3,5-dione of particular structure and at least one self-tanning agent.

The present invention also relates to a cosmetic treatment process for artificially tanning or browning the skin and to the use of at least one derivative or a mixture of derivatives of 1,7-bisphenyl heptane-3,5-dione of particular structure for improving the coloration and/or stability of a self-tanning agent.

The invention also relates to the uses of these compositions for giving the skin a coloration close to that of a natural skin tan.

For the purposes of the present patent application, the term "self-tanning agent" means an agent which, when applied to the skin, especially to the face, gives a tanning effect that is more or less similar in appearance to that which may result from prolonged exposure to sunlight (natural tan) or under a UV lamp.

2. Description of the Prior Art

Nowadays, it is important to have a healthy appearance and tanned skin is always a sign of good health. However, natural tanning is not always desirable since it requires prolonged exposure to UV radiation, in particular to UV-A radiation which causes tanning of the skin, but on the other hand is liable to induce reactions or even impairment of the skin, especially in the case of sensitive skin or skin that is continually exposed to solar radiation: erythema, burns, loss of elasticity, appearance of wrinkles, premature aging. It is thus desirable to find an alternative to natural tanning, which is compatible with the requirements of such skin.

Most of the cosmetic products intended for artificially tanning the skin are based on carbonyl derivatives allowing, by interaction with the amino acids of the skin, the formation of colored products, among which mention is made of mono- or polycarbonyl compounds such as, for example, isatin, alloxan, ninhydrin, glyceraldehyde, mesotartaric aldehyde, glutaraldehyde, erythrulose and dihydroxyacetone (DHA).

DHA is a particularly advantageous product that is commonly used in cosmetics as an agent for artificially tanning the skin; when applied to the skin, especially to the face, it gives a tanning or browning effect that is similar in appearance to that which may result from prolonged exposure to sunlight (natural tanning) or under a UV lamp.

One drawback of DHA is the slow speed at which the coloration develops: in point of fact, it takes several hours (3 to 5 hours in general) for the coloration to be developed. The intensity of the coloration obtained on the skin and/or its staying power over time (resistance to washing) and/or the speed at which the coloration develops are often considered insufficient by the users of DHA-based self-tanning compositions.

Another problem posed by DHA-based compositions is that they have the annoying tendency, which is more or less pronounced depending on the nature of the medium in which they are formulated, of degrading over time. These problems associated with the storage and/or conservation of DHA-based compositions are generally reflected in the end by an undesirable yellowing of these compositions.

There is thus increasing demand for fast-acting self-tanning products that give a coloration close to that of a natural tan.

SUMMARY OF THE INVENTION

Surprisingly and advantageously, the Applicant has found that the use of at least one derivative or a mixture of derivatives of 1,7-bisphenyl heptane-3,5-dione of particular structure of formula (I) as defined below improves the stability and/or coloration of compositions comprising a self-tanning agent. The colorations obtained are more chromatic, more stable over time and show good homogeneity.

The composition according to the present invention comprises, in a cosmetically acceptable support, at least one derivative or a mixture of derivatives of 1,7-bisphenyl heptane-3,5-dione of particular structure of formula (I) as defined below and at least one self-tanning agent.

A subject of the present patent application is also the use of the composition according to the invention as a composition for tanning or browning the skin; and a cosmetic process for tanning or browning the skin such that it consists in applying to the skin an effective amount of a composition according to the invention.

Finally, the present patent application also relates to the use of at least one derivative or a mixture of derivatives of 1,7-bisphenyl heptane-3,5-dione of particular structure of formula (I) as defined below in compositions for artificially tanning and/or browning the skin, containing at least one self-tanning agent, in order to improve the coloration and/or stability of the said self-tanning agent.

Other characteristics, aspects and advantages of the present invention will become apparent on reading the detailed description that follows.

DETAILED DESCRIPTION OF BEST MODE AND SPECIFIC/PREFERRED EMBODIMENTS OF THE INVENTION

The 1,7-bisphenyl heptane-3,5-dione derivatives in accordance with the invention correspond to formula (I) below:

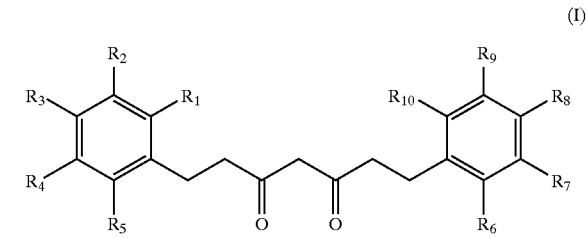

(I)

in which:

$R_1$, $R_2$, $R_3$, $R_4$, $R_5$, $R_6$, $R_7$, $R_8$, $R_9$ and $R_{10}$, which may be identical or different, are chosen from:

(i) a hydrogen atom;
(ii) a linear or branched $C_1$–$C_4$ alkyl radical;
(iii) a radical $OR_{11}$ in which $R_{11}$ is chosen from a hydrogen atom, a linear or branched $C_1$–$C_4$ alkyl radical, a radical $PO(OX_1)(OX_2)$ or a radical $SO_2(OX_3)$ in which $X_1$, $X_2$ and $X_3$, which may be identical or different, denote a hydrogen atom or an alkali metal cation or $NH_4^+$, $X_1$ and $X_2$ together also possibly denoting a divalent metal cation;
(iv) an acyl radical $R_{12}CO$ in which $R_{12}$ is chosen from $C_1$–$C_{30}$ hydrocarbon-based radicals, which are linear or branched, saturated or unsaturated, hydroxylated or non-hydroxylated, and carboxylated or non-carboxylated;
(v) a glycosyl or uronyl radical;
when a radical $R_1$ to $R_{10}$ denotes a residue $OR_{11}$, it may also form, with the aromatic ring to which it is attached and an adjacent radical, a ring containing 5 or 6 atoms;
it being understood that at least one of the radicals $R_1$ to $R_{10}$ denotes a residue $OR_{11}$.

In formula (I) described above, the alkyl radicals may especially denote methyl, ethyl, propyl, isopropyl, n-propyl, butyl, n-butyl and tert-butyl radicals; the alkyl radical preferably denotes a methyl radical.

In formula (I) described above, the glycosyl radical more particularly denotes a glucosyl radical.

In formula (I) described above, the uronyl radical more particularly denotes a mannuronyl or glucuronyl radical.

The compounds of formula (I) are known per se. The tetrahydrocurcuminoids in accordance with the invention are obtained by reducing curcumin or synthesized as described in the articles "Synthesis and antibacterial activity of tetrahydrocurcuminoids; S. Venkateswarlu, M. Rambabu, G. V. Subbaraju and S. Satyanarayana; Asian Journal of Chemistry, 2000, 1, 141–144", "Synthesis of naturally occurring curcuminoids and related compounds; U. Pedersen, P. B. Rasmussen, S. O. Lawesson; Liebigs Ann. Chem., 1985, 1557–1569", patent applications JP 02 051 595, JP 02 069 431, JP 02 049 747 and JP 02 128 133, patent U.S. Pat. No. 5,266,344 and patent application WO 00/61162.

Among the compounds of formula (I) that are preferred according to the present invention, mention may be made of:
-1,7-bis(3-hydroxy-4-methoxyphenyl)heptane-3,5-dione or tetrahydrocurcumin (THC) of structure:

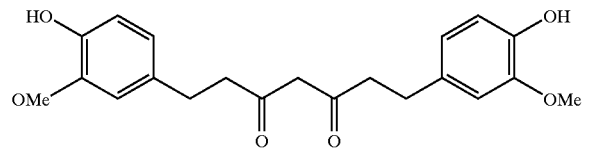

-1-(3-methoxy-4-hydroxyphenyl)-7-(4'-hydroxyphenyl)heptane-3,5-dione or tetrahydrodemethoxycurcumin (THDC) of structure:

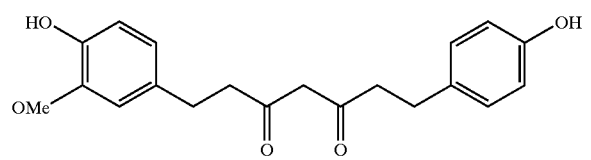

-1,7-bis(4-hydroxyphenyl)heptane-3,5-dione or tetrahydrobis(demethoxy)curcumin (THBDC) of structure:

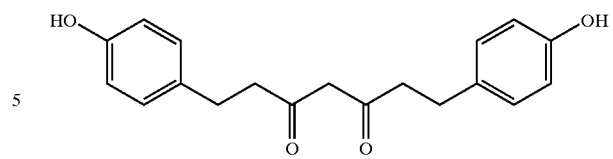

-1,7-bis(3,4-dihydroxyphenyl)heptane-3,5-dione of structure:

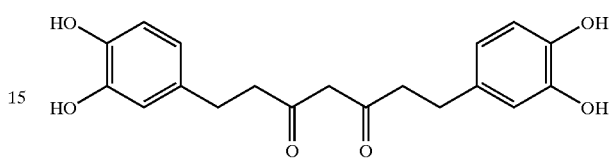

and also mixtures thereof.

One particular form of the invention consists in using as sole compound of formula (I) 1,7-bis(3-hydroxy-4-methoxyphenyl)heptane-3,5-dione or tetrahydrocurcumin (THC).

Another particular form of the invention consists in using a mixture of compounds of formula (I) consisting of:
tetrahydrocurcumin,
tetrahydrodemethoxycurcumin, and
tetrahydrobis(demethoxy)curcumin.

A mixture consisting of:
70% to 95% by weight of tetrahydrocurcumin,
4% to 25% by weight of tetrahydrodemethoxycurcumin, and
0.5% to 10% by weight of tetrahydrobis(demethoxy)-curcumin;
will be used more particularly, and even more particularly a mixture consisting of:
75% to 90% by weight of tetrahydrocurcumin,
8% to 20% by weight of tetrahydrodemethoxycurcumin, and
1% to 5% by weight of tetrahydrobis(demethoxy) curcumin for instance the product described and synthesized in patent application WO 00/61162 and sold by the company Sabinsa Corporation under the trademark Tetrahydrocurcuminoids CG or Tetrahydrocurcuminoids.

In general, the compound(s) of formula (I) present in the composition is (are) totally dissolved in the support for the composition.

The compounds of formula (I) according to the invention preferably represent from 0.001% to 10% by weight approximately relative to the total weight of the cosmetic composition, more particularly from 0.01% to 5% and even more preferably from 0.1% to 5% by weight approximately relative to this weight.

The self-tanning agents are generally chosen from mono- or polycarbonyl compounds such as, for example, isatin, alloxan, ninhydrin, glyceraldehyde, mesotartaric aldehyde, glutaraldehyde, erythrulose, pyrazoline-4,5-dione derivatives as described in patent application FR-2,466,492 and WO 97/35842, dihydroxyacetone (DHA), and 4,4-dihydroxypyrazolin-5-one derivatives as described in patent application EP-903,342. DHA will preferably be used.

DHA may be used in free form and/or encapsulated, for example in lipid vesicles such as liposomes, described especially in patent application WO 97/25970.

These self-tanning agents may be combined with at least one synthetic or natural direct dye and/or at least one indole derivative, for instance those described in patents EP-425,324 and EP-456,545.

These self-tanning agents may also be combined with other synthetic or natural skin colorants.

For the purposes of the present invention, the term "skin colorant" will mean any compound with particular affinity for the skin, making it possible to give the skin a long-lasting, non-covering (i.e., not having a tendency to opacify the skin) coloration and which is not removed either with water or using a solvent, and which is resistant both to rubbing and to washing with a solution containing surfactants. Such a long-lasting coloration is thus distinguished from the superficial and transient coloration provided, for example, by a makeup pigment.

The additional colorants may also be chosen, for example, from plant extracts such as, for example, the "insoluble" extracts of redwoods of the genus *Pterocarpus* and of the genus *Baphia*, for instance *Pterocarpus santalinus, Pterocarpus osun, Pterocarpus soyauxii, Pterocarpus erinaceus, Pterocarpus indicus* or *Baphia nitida*, for instance those described in patent application EP-971,683.

The additional colorants may also be chosen, for example, from other plant extracts such as, for example, the sorghum extracts obtained from the whole plant, the stems, the seeds or the leaves of the genus *Sorghum*. The preferred species of *Sorghum* are chosen from *Sorghum bicolor, Sorghum caudatum, Sorghum nervosum, Sorghum durra, Sorghum vulgare* and *Sorghum* plants in combination with *Colletotrichum graminicola*, for instance those described in patent application FR-0-200,251.

The colorants may also be iron oxide nanopigments, the mean size of the elementary particles of which is less than 100 nm, such as those described in patent application EP-966,953.

The self-tanning agents are generally present in the compositions according to the invention in proportions ranging from 0.1% to 10% by weight relative to the total weight of the composition, and preferably from 0.2% to 8% by weight relative to the total weight of the composition.

The self-tanning compositions in accordance with the invention may be in the form of creams, milks, gels, cream-gels, oil-in-water emulsions, vesicular dispersions, fluid lotions, in particular vaporizable fluid lotions, or any other form generally used in cosmetics, in particular those usually suitable for self-tanning cosmetic compositions.

The compositions in accordance with the present invention may also comprise standard cosmetic adjuvants, especially a cosmetic adjuvant chosen from fatty substances, organic solvents, ionic or nonionic thickeners, softeners, humectants, opacifiers, stabilizers, emollients, silicones, antifoams, insect repellants, fragrances, preserving agents, anionic, cationic, nonionic, zwitterionic or amphoteric surfactants, substance P antagonists, CGRP antagonists, fillers, polymers, propellants, acidifying or basifying agents or any other ingredient usually used in cosmetics and/or dermatology, in particular for the manufacture of self-tanning compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally greater than 35° C.

Oils that may be mentioned include mineral oils (paraffin); plant oils (sweet almond oil, macadamia oil, blackcurrant pip oil, jojoba oil); synthetic oils, for instance perhydrosqualene, fatty alcohols, fatty acids or fatty esters (for instance the $C_{12}$–$C_{15}$ alkyl benzoate sold under the trademark "Finsolv TN" by the company Finetex, octyl palmitate, isopropyl lanolate, triglycerides, including those of capric/caprylic acids, oxyethylenated or oxypropylenated fatty esters and ethers; silicone oils (cyclomethicone, polydimethylsiloxanes or PDMS) or fluoro oils; polyalkylenes, and mixtures thereof.

Waxy compounds that may be mentioned include paraffin, carnauba wax, beeswax and hydrogenated castor oil.

Among the organic solvents that may be mentioned are lower alcohols and polyols containing up to 8 carbon atoms.

The thickeners may be chosen especially from crosslinked polyacrylic acids, and modified or unmodified guar gums and celluloses, such as hydroxypropyl guar gum, methylhydroxyethylcellulose and hydroxypropylmethylcellulose.

The compositions in accordance with the invention may also comprise at least one organic photoprotective agent and/or at least one mineral photoprotective agent that is (are) UVA-active and/or UVB-active (absorbent) and that is (are) water-soluble or liposoluble or even insoluble in the cosmetic solvents commonly used.

The ultraviolet-screening agents may be chosen from organic UV-screening agents and mineral UV-screening agents, or mixtures thereof.

The organic UV-screening agents in accordance with the invention may be water-soluble, liposoluble or insoluble in the usual cosmetic solvents. They are chosen especially from anthranilates; cinnamic derivatives; dibenzoylmethane derivatives; salicylic derivatives; camphor derivatives; triazine derivatives such as those described in patent applications U.S. Pat. No. 4,367,390, EP-863,145, EP-517,104, EP-570,838, EP-796,851, EP-775,698, EP-878,469 and EP-933,376,; benzophenone derivatives, especially those described in patent applications EP-A-1,046,391 and DE-100,12,408; β,β'-diphenylacrylate derivatives; benzotriazole derivatives; benzimidazole derivatives; imidazolines; bis-benzazolyl derivatives as described in patents EP-669,323 and U.S. Pat. No. 2,463,264; p-aminobenzoic acid (PABA) derivatives; methylenebis (hydroxyphenylbenzotriazole) derivatives as described in patent applications U.S. Pat. Nos. 5,237,071, 5,166,355, GB-2,303,549, DE-197,26,184 and EP-893,119; screening polymers and screening silicones such as those described especially in patent application WO 93/04665; dimers derived from α-alkylstyrene, such as those described in patent application DE-198,55,649, 4,4-diarylbutadiene derivatives such as those described in patent applications EP-0-967,200, DE-197,55,649 and EP-133,981; amino-substituted hydroxybenzophenones such as the structures described in EP-1-046,391 and EP-1-133,980; and mixtures thereof.

As examples of organic screening agents, mention may be made of the following, denoted hereinbelow under their INCI name:

Para-Aminobenzoic Acid Derivatives:

PABA,

Ethyl PABA,

Ethyl dihydroxypropyl PABA,

Ethylhexyl dimethyl PABA sold in particular under the name "Escalol 507" by ISP, Glyceryl PABA, PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo 20 Heliopan OS" by Haarmann and Reimer,
Dipropylene glycol salicylate sold under the name "Dipsal" by Scher,
TEA salicylate sold under the name "Neo Heliopan TS" by Haarmann and Reimer.
Dibenzoylmethane Derivatives:
Butyl methoxydibenzoylmethane sold in particular under the trademark "Parsol 1789" by Hoffmann LaRoche,
Isopropyldibenzoylmethane.
Cinnamic Derivatives:
Ethylhexyl methoxycinnamate sold in particular under the trademark "Parsol MCX" by Hoffmann LaRoche,
Isopropyl methoxycinnamate,
Isoamyl methoxycinnamate sold under the trademark "Neo Heliopan E 1000" by Haarmann and Reimer,
Cinoxate,
DEA methoxycinnamate,
Diisopropyl methoxycinnamate,
Glyceryl ethylhexanoate dimethoxycinnamate.
β,β'-Diphenylacrylate Derivatives:
Octocrylene sold in particular under the trademark "Uvinul N539" by BASF
Etocrylene sold in particular under the trademark "Uvinul N35" by BASF.
Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12
n-hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulphonic acid manufactured under the name "Mexoryl SL" by Chimex,
Camphor benzalkonium methosulphate manufactured under the name "Mexoryl SO" by Chimex,
Terephthalylidenedicamphorsulphonic acid manufactured under the name "Mexoryl SX" by Chimex,
Polyacrylamidomethylbenzylidenecamphor manufactured under the name "Mexoryl SW" by Chimex.
Phenylbenzimidazole Derivatives:
Phenylbenzimidazolesulphonic acid sold in particular under the trademark "Eusolex 232" by Merck,
Disodium phenyl dibenzimidazole tetrasulphonate, sold under the trademark "Neo Heliopan AP" by Haarmann and Reimer.
Triazine Derivatives:
Anisotriazine sold under the trademark "Tinosorb S" by Ciba Geigy
Ethylhexyltriazone sold in particular under the trademark "Uvinul T150" by BASF,
Diethylhexylbutamidotriazone sold under the trademark "Uvasorb HEB" by Sigma 3V.
Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trademark "MIXXIM BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxane containing benzalmalonate functions, as Polysilicone-15 sold under the trademark "Parsol SLX" by Hoffmann LaRoche.
4,4-diarylbutadiene Derivatives:
1,1-dicarboxy (2,2'-diméthyl-propyl)-4,4-diphénylbutadiène and mixtures thereof.
The organic UV-screening agents that are more particularly preferred are chosen from the following compounds:
Ethylhexyl salicylate,
Butylmethoxydibenzoylmethane,
Ethylhexyl methoxycinnamate,
Octocrylene,
Phenylbenzimidazolesulphonic acid,
Terephthalylidenedicamphorsulphonic acid,
Benzophenone-3,
Benzophenone-4,
Benzophenone-5,
n-hexyl 2-(4-diethylamino-2-hydroxybenzoyl)benzoate,
4-Methylbenzylidenecamphor,
Benzimidazilate,
Anisotriazine,
Ethylhexyltriazone,
Diethylhexylbutamidotriazone,
Methylenebis(benzotriazolyl)tetramethylbutyl-phenol,
Drometrizole trisiloxane, and mixtures thereof.

The mineral photoprotective agents are chosen from pigments or nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, and mixtures thereof. Standard coating agents are, moreover, alumina and/or aluminum stearate. Such coated or uncoated metal oxide nanopigments are described in particular in patent applications EP-518,772 and EP-518,773.

The photoprotective agents are generally present in the compositions according to the invention in proportions ranging from 0.1% to 20% by weight relative to the total weight of the composition, and preferably ranging from 0.2% to 15% by weight relative to the total weight of the composition.

Needless to say, a person skilled in the art will take care to select the abovementioned optional additional compound (s) and/or the amounts thereof such that the advantageous properties intrinsically associated with the combination in accordance with the invention are not, or are not substantially, adversely affected by the envisaged addition (s).

The compositions according to the invention may be prepared according to techniques that are well known to those skilled in the art, in particular those intended for preparing emulsions of oil-in-water or water-in-oil type.

This composition may be in particular in the form of a simple or complex emulsion (O/W, W/O, O/W/O or W/O/W emulsion) such as a cream or a milk, or in the form of a gel or a cream-gel, in the form of a lotion, a powder or a solid tube, and may optionally be packaged as an aerosol and be in the form of a mousse or a spray.

Preferably, the compositions according to the invention are in the form of an oil-in-water or water-in-oil emulsion.

When it is an emulsion, the aqueous phase of this emulsion may comprise a nonionic vesicular dispersion prepared according to known processes (Bangham, Standish and Watkins, J. Mol. Biol. 13, 238 (1965), FR-2,315,991 and FR-2,416,008).

The invention also relates to a cosmetic treatment process for artificially tanning and/or browning the skin, characterized in that it consists in applying to the skin an effective amount of a cosmetic composition as defined above.

The invention also relates to the use of at least one derivative or a mixture of derivatives of 1,7-bisphenyl heptane-3,5-dione of formula (I) as defined above, with the aim of improving the coloration and/or stability of a self-tanning agent such as those defined above, contained in a cosmetic composition for artificially tanning and/or browning the skin.

In order to further illustrate the present invention and the advantages thereof, the following specific examples are given, it being understood that same are intended only as illustrative and in nowise limitative.

In the composition below, the amounts are expressed in grams.

TABLE I

| COMPOSITION OF THE INVENTION | AMOUNT (GRAMS) |
|---|---|
| Hydroxypropylmethylcellulose | 2 |
| Glycerol | 5 |
| Propylene glycol | 10 |
| Absolute ethanol | 10 |
| Dihydroxyacetone | 4 |
| Mixture of tetrahydrocurcuminoids of formula (I) (Tetrahydrocurcuminoids CG from Sabinsa) | 1 |
| Demineralized water qs | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for the artificial tanning or browning of human skin, comprising (a) at least one self-tanning agent and (b) at least one tetrahydrocurcumin compound or derivative thereof, formulated into (c) a topically applicable cosmetically/dermatologically acceptable support therefor.

2. The cosmetic/dermatological composition as defined by claim 1, said at least one tetrahydrocurcumin compound or derivative thereof comprising a 1,7-diphenyl-3,5-heptanedione having the following structural formula (I):

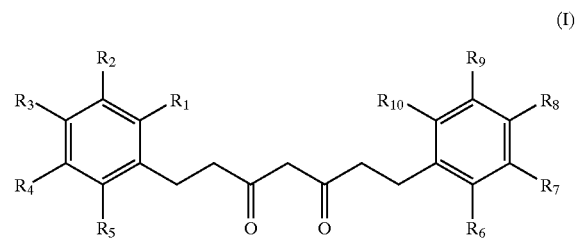

in which the radicals $R_1$, $R_2$, $R_3$, $R_4$, $R_5$, $R_6$, $R_7$, $R_8$, $R_9$ and $R_{10}$, which may identical or different, are each (i) a hydrogen atom; (ii) a linear or branched $C_1$–$C_4$ alkyl radical; (iii) a radical $OR_{11}$ in which $R_{11}$ is a hydrogen atom, a linear or branched $C_1$–$C_4$ alkyl radical, a radical $PO(OX_1)(OX_2)$ or a radical $SO_2(OX_3)$ in which $X_1$, $X_2$ and $X_3$, which may be identical or different, are each a hydrogen atom or an alkali metal cation or $NH_4^+$, with the proviso that $X_1$ and $X_2$ may together be a divalent metal cation; (iv) an acyl radical $R_{12}CO$ in which $R_{12}$ is a $C_1$–$C_{30}$ hydrocarbon radical, which may be linear or branched, saturated or unsaturated, hydroxylated or nonhydroxylated, carboxylated or noncarboxylated; (v) a glycosyl or uronyl radical; with the proviso that, when a radical $R_1$ to $R_{10}$ is a radical $OR_{11}$, it can also form with the aromatic ring to which it is bonded and an adjacent radical a ring member containing 5 or 6 atoms; with the proviso that the radicals $OR_3$ and $OR_8$ may together form with the aromatic ring to which they are bonded and the radicals $R_2$ or $R_4$ and $R_7$ or $R_9$ a ring member containing 5 or 6 atoms; and with the further proviso that at least one of the radicals $R_1$ to $R_{10}$ is a radical $OR_{11}$.

3. The cosmetic/dermatological composition as defined by claim 2, said at least one compound of formula (I) being selected from the group consisting of:

(a) 1,7-bis(3-methoxy-4-hydroxyphenyl)heptane-3,5-dione or tetrahydrocurcumin (THC) having the structure:

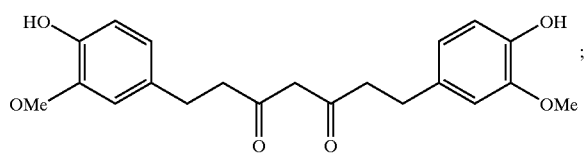

(b) 1-(3-methoxy-4-hydroxyphenyl)-7-(4'-hydroxyphenyl) heptane-3,5-dione or tetrahydrodemethoxycurcumin (THDC) having the structure:

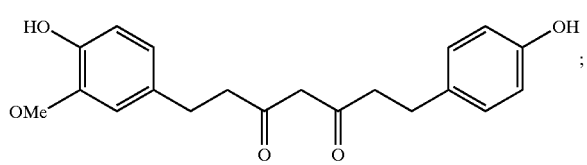

(c) 1,7-bis(4-hydroxyphenyl)heptane-3,5-dione or tetrahydrobisdemethoxycurcumin (THBDC) having the structure:

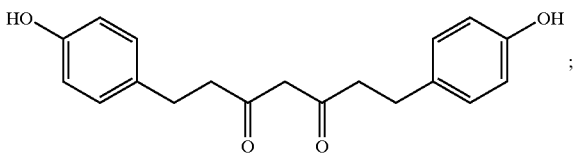

(d) 1,7-bis(3,4-dihydroxyphenyl)heptane-3,5-dione having the structure:

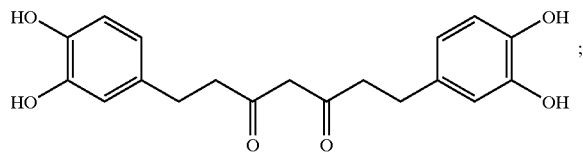

and (e) also mixtures thereof.

4. The cosmetic/dermatological composition as defined by claim 3, said at least one compound of formula (I) solely being 1,7-bis(3-methoxy-4-hydroxyphenyl)heptane-3,5-dione or tetrahydrocurcumin (THC).

5. The cosmetic/dermatological composition as defined by claim 2, said at least one compound of formula (I) comprising a mixture of tetrahydrocurcumin, tetrahydrodemethoxycurcumin, and tetrahydrobis(demethoxy)curcumin.

6. The cosmetic/dermatological composition as defined by claim 5, said at least one compound of formula (I) comprising a mixture of 70% to 95% by weight of tetrahydrocurcumin, 4% to 25% by weight of tetrahydrodemethoxycurcumin, and 0.5% to 10% by weight of tetrahydrobis(demethoxy)curcumin.

7. The cosmetic/dermatological composition as defined by claim 6, said at least one compound of formula (I) comprising a mixture of 75% to 90% by weight of tetrahydrocurcumin, 8% to 20% by weight of tetrahydrodemethoxycurcumin, and 1% to 5% by weight of tetrahydrobis(demethoxy)-curcumin.

8. The cosmetic/dermatological composition as defined by claim 2, said at least one compound of formula (I) comprising from 0.001% to 10% by weight thereof.

9. The cosmetic/dermatological composition as defined by claim 2, said at least one compound of formula (I) comprising from 0.01% to 5% by weight thereof.

10. The cosmetic/dermatological composition as defined by claim 2, said at least one compound of formula (I) comprising from 0.1% to 5% by weight thereof.

11. The cosmetic/dermatological composition as defined by claim 1, said at least one self-tanning agent comprising a mono- or polycarbonyl compound.

12. The cosmetic/dermatological composition as defined by claim 11, said at least one self-tanning agent being selected from the group consisting of isatin, alloxan, ninhydrin, glyceraldehyde, mesotartaric aldehyde, glutaraldehyde, erythrulose, pyrazoline-4,5-dione derivatives, dihydroxyacetone (DHA) and 4,4-dihydroxypyrazoline-5-dione derivatives.

13. The cosmetic/dermatological composition as defined by claim 12, said at least one self-tanning agent comprising DHA.

14. The cosmetic/dermatological composition as defined by claim 1, said at least one self-tanning agent comprising from 0.1% to 10% by weight thereof.

15. The cosmetic/dermatological composition as defined by claim 1, comprising at least one synthetic or natural direct dye, and/or at least one indole derivative.

16. The cosmetic/dermatological composition as defined by claim 1, further comprising an "insoluble" extract of redwoods of the genus *Pterocarpus* and of the genus *Baphia*.

17. The cosmetic/dermatological composition as defined by claim 1, further comprising iron oxide nanopigments, the mean size of the elementary particles of which is less than 100 nm.

18. The cosmetic/dermatological composition as defined by claim 1, further comprising at least one fatty substance, organic solvent, ionic or nonionic thickener, softener, humectant, opacifier, stabilizer, emollient, silicone, antifoam, insect repellant, fragrance, preservative, anionic, cationic, nonionic, zwitterionic or amphoteric surfactant, substance P antagonist, CGRP antagonist, filler, polymer, propellant, acidifying or basifying agent or any other conventional cosmetics and/or dermatology additive or adjuvant.

19. The cosmetic/dermatological composition as defined by claim 1, further comprising at least one organic photoprotective agent and/or at least one mineral photoprotective agent that is (are) UVA-active and/or UVB-active.

20. The cosmetic/dermatological composition as defined by claim 19, comprising at least one organic photoprotective agent selected from the group consisting of anthranilates; cinnamic derivatives; dibenzoylmethane derivatives; salicylic derivatives; camphor derivatives; triazine derivatives; benzophenone derivatives; $\beta,\beta'$-diphenylacrylate derivatives; benzotriazole derivatives; benzimidazole derivatives; imidazolines; bis-benzazolyl derivatives; p-aminobenzoic acid (PABA) derivatives; methylenebis(hydroxyphenylbenzotriazole) derivatives; screening polymers and screening silicones; dimers derived from $\alpha$-alkylstyrene; 4,4-diarybutadiene derivatives; amino-substituted hydroxybenzophenones; and mixtures thereof.

21. The cosmetic/dermatological composition as defined by claim 20, said at least one organic photoprotective agent being selected from the group consisting of:

Ethylhexyl salicylate,
Butylmethoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
n-hexyl 2-(4-diethylamino-2-hydroxybenzoyl)benzoate,
4-Methylbenzylidenecamphor,
Disodium phenyl dibenzimidazole tetrasulfonate,
Anisotriazine,
Ethylhexyltriazone,
Diethylhexylbutamidotriazone, Methylenebis(benzotriazolyl)tetramethylbutyl-phenol,
Drometrizole trisiloxane,
Polysilicone-15
1,1-dicarboxy (2,2'-diméthyl-propyl)-4,4-diphénylbutadiène, and mixtures thereof.

22. The cosmetic/dermatological composition as defined by claim 19, comprising at least one mineral photoprotective agent selected from the group consisting of coated or uncoated metal oxide pigments or nanopigments.

23. The cosmetic/dermatological composition as defined by claim 22, said at least one mineral photoprotective agent being selected from the group consisting of coated or uncoated nanopigments of titanium oxide, of iron oxide, of zinc oxide, of zirconium oxide or of cerium oxide, and mixtures thereof.

24. The cosmetic/dermatological composition as defined by claim 19, said at least one photoprotective agent comprising from 0.1% to 20% by weight thereof.

25. The cosmetic/dermatological composition as defined by claim 19, said at least one of photoprotective agent comprising from 0.2% to 15% by weight thereof.

26. The cosmetic/dermatological composition as defined by claim 1, formulated as a nonionic vesicular dispersion, an emulsion, an emulsion of water-in-oil type, of oil-in-water type, a cream or a triple emulsion (W/O/W or O/W/O emulsion), a milk, a gel, a cream-gel, a suspension, a dispersion, a mousse or a spray.

27. A regime or regimen for the artificial tanning or browning of human skin, comprising topically applying thereon a thus effective amount of the cosmetic/dermatological composition as defined by claim 1.

28. A method for improving the coloration and/or stability of at least one self-tanning agent, comprising formulating therewith at least one tetrahydrocurcumin compound or derivative thereof.

* * * * *